United States Patent
Sacherer

(10) Patent No.: US 12,336,925 B2
(45) Date of Patent: Jun. 24, 2025

(54) ORTHOSIS JOINT

(71) Applicant: OTTOBOCK SE & CO. KGAA, Duderstadt (DE)

(72) Inventor: Bernhard Sacherer, Friesenheim (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 315 days.

(21) Appl. No.: 17/905,078

(22) PCT Filed: Feb. 24, 2021

(86) PCT No.: PCT/EP2021/025075
§ 371 (c)(1),
(2) Date: Aug. 26, 2022

(87) PCT Pub. No.: WO2021/170296
PCT Pub. Date: Sep. 2, 2021

(65) Prior Publication Data
US 2022/0409416 A1 Dec. 29, 2022

(30) Foreign Application Priority Data
Feb. 28, 2020 (DE) ...................... 10 2020 001 327.9

(51) Int. Cl.
*A61F 5/01* (2006.01)
(52) U.S. Cl.
CPC .... *A61F 5/0125* (2013.01); *A61F 2005/0179* (2013.01)
(58) Field of Classification Search
CPC ............ A61F 5/0102; A61F 5/012–013; A61F 2005/0132–0188; A61F 2005/0197; A61F 5/01–0195; A61F 5/04; A61F 5/042; A61F 5/058–05875; A61F 5/10; A61F 5/11; A63B 21/4011; A63B 21/4023; A63B 21/4025; A61H 1/02; A61H 1/0237; A61H 1/024; A61H 1/0262; A61H 3/00
See application file for complete search history.

(56) References Cited

U.S. PATENT DOCUMENTS

| | | | |
|---|---|---|---|
| 3,928,872 A * | 12/1975 | Johnson | A61F 5/0106 2/22 |
| 4,865,024 A | 9/1989 | Hensley et al. | |
| 5,437,619 A * | 8/1995 | Malewicz | A61F 5/013 602/5 |
| 7,192,407 B2 | 3/2007 | Seligman et al. | |

(Continued)

FOREIGN PATENT DOCUMENTS

| | | |
|---|---|---|
| DE | 20 2011 004 130 U1 | 6/2011 |
| DE | 10 2013 011 382 A1 | 1/2015 |

(Continued)

*Primary Examiner* — Michelle J Lee
(74) *Attorney, Agent, or Firm* — WCF IP

(57) ABSTRACT

The invention relates to an orthosis joint (5), in particular for forming a functional angle (14) for a deflection on both sides, comprising: a first joint arm (1) and a second joint arm (2) that are mounted on a shaft (7) such that they can be pivoted relative to each other; and at least one functional element (29) that functions as a retractive element between the two joint arms (1, 2) and comprises at least one spring (16, 17) subjected to bending which produces a retractive force (27) on both sides when the joint arms (1, 2) are deflected.

8 Claims, 2 Drawing Sheets

(56) References Cited

U.S. PATENT DOCUMENTS

Figure 1:
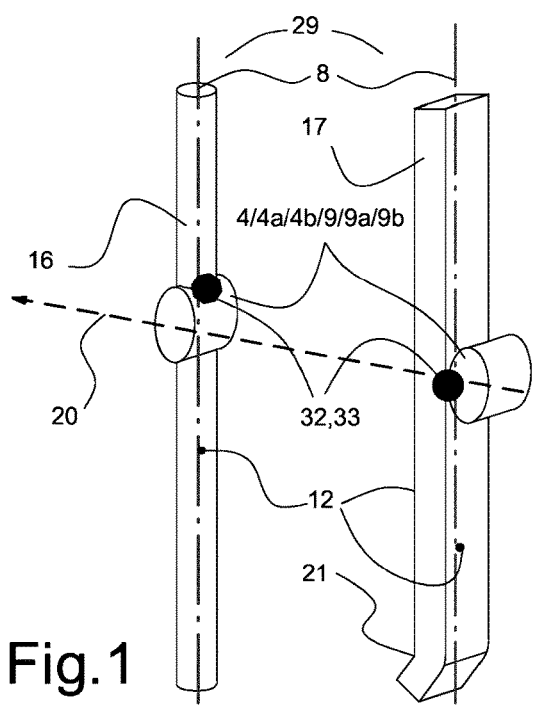

2004/0153015 A1* 8/2004 Seligman .............. A61F 5/0123
602/16
2006/0116616 A1 6/2006 Albrecht et al.
2019/0336385 A1* 11/2019 Soucy ..................... A61H 3/00

FOREIGN PATENT DOCUMENTS

DE    10 2016 107 779 A1   11/2017
EP         1 768 620 B1    8/2011
EP           17686201 B1    8/2011
WO   WO-2019170803 A1 *  9/2019   ........... A61F 5/0123

* cited by examiner

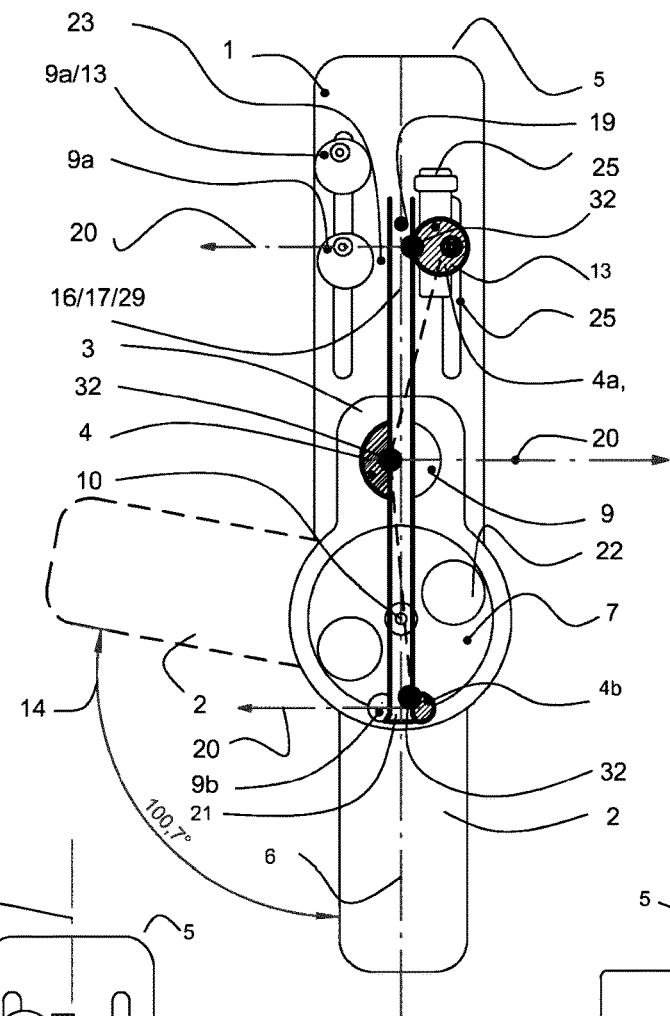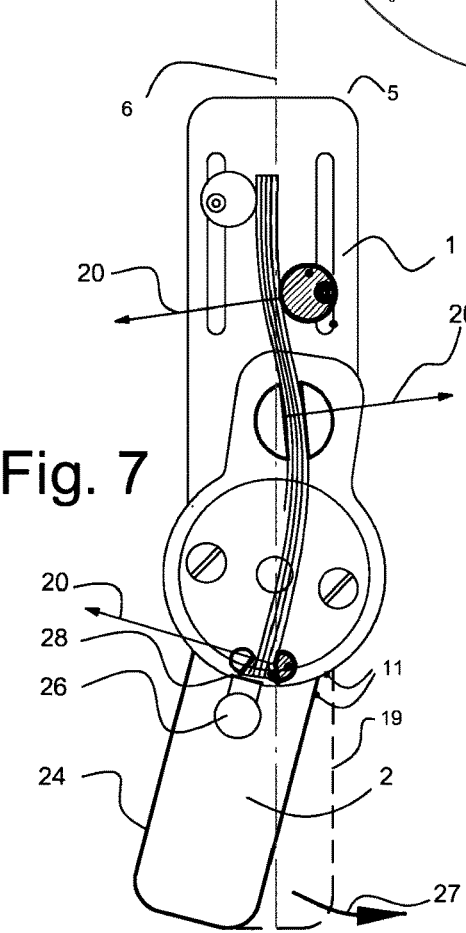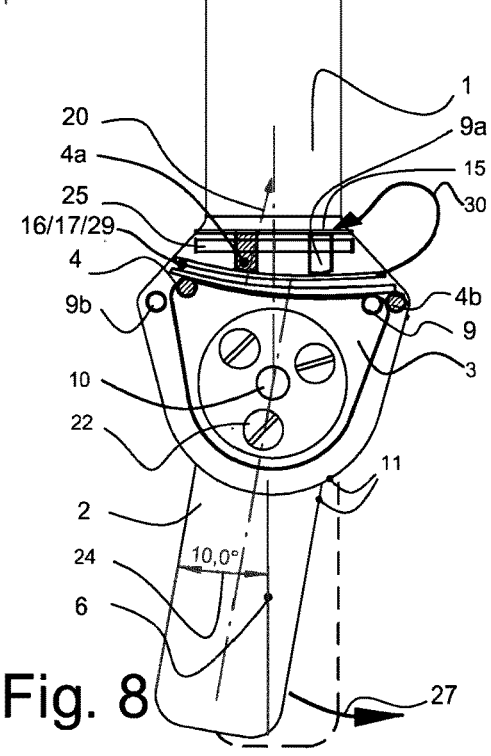

ORTHOSIS JOINT

The invention relates to an orthosis joint, especially for a leg joint, e.g. a hip, knee or ankle joint, or an arm joint, such as a shoulder, elbow or wrist joint, with a first joint arm and a second joint arm that are connected to each other such that they can be pivoted relative to each other, in particular with deflection on either side and with at least one functional element that acts as a restoring element between the joint arms.

Such an orthosis joint can be used to particular advantage on orthoses for the lower extremities, such as an ankle-foot orthosis (AFO) or a knee-ankle-foot orthosis (KAFO). However, it is not limited to this area or purpose and it can theoretically also be used as a prosthetic joint.

In principle, it is also possible to use a joint of this type, e.g., in a positioning therapy, especially in the area of the upper extremities.

The movement in a body joint can be supported with orthosis joints or restricted to protect the body joint, if this makes sense from a therapeutic point of view. During movement restriction, the orthosis joint forms an end stop for the body joint, whereby a resistance in the orthosis joint should rise as gently as possible up to the end stop, which then acts on the natural body joint and limits the deflection of the body joint.

For the resistance, an orthosis joint can be used to generate a restoring force that returns the body joint to an initial position. There is no restoring force in the initial position. When the body joint is deflected from this starting position, the restoring force in the orthosis joint preferably increases. The initial position is also referred to as the basic position.

In an orthosis joint that operates with a restoring force, the joint arms are usually set to a basic position that corresponds to that of the body joint, forming an angle between the first and second joint arms.

Such an orthosis joint with a basic position and a restoring force for deflections on either side is disclosed in DE 20 2011 004 130 U1. As a functional element, this design uses two stacks of disc spring laterally attached to an upper joint arm, which are accommodated in two housings and which generate a strong restoring force when the joint arms are deflected.

To set a maximum functional angle by which the two joint arms can be pivoted against each other from the basic position during use of the orthosis, an adjusting element with an end stop surface is provided on each stack of disc springs so that the lower joint arm which is provided with a foot stirrup shell, can only be pivoted in a limited angular range relative to the upper joint arm.

Different spring properties are provided by interchangeable preconfigured spring modules. Fine adjustment of the maximum spring force is possible to a small extent by preloading the stack of disc springs. However, spring deflection is lost and a minimum force may also be increased.

Similar designs can be found to an extent in DE 10 2016 107 779 A1 or DE 10 2013 011 382 A1 with two spring-loaded functional elements on both sides of an upper joint arm e.g. of an ankle joint. A lower joint arm is, for example, a foot stirrup shell that can be arranged on a foot. Depending on the direction of the deflection possible in both directions, one of the two functional elements is controlled to generate a restoring force. To adjust the restoring forces, the functional elements and, if necessary, the housings can be removed and replaced. A wide range of different functional elements is available for different requirements.

The problem with all previously known designs is that when the joint is pivoted from one direction beyond the basic position in the other direction, the restoring forces generated by the functional elements drop and rise abruptly during the transition or during the alternating phase of the deflections in the opposite directions. Exactly in this movement phase, however, a natural joint not only tilts back and forth without resistance, i.e. without a restoring force, but also has gently, i.e. jerk-free, decreasing and increasing restoring forces of the muscles and the ligaments.

In contrast, the orthosis joints of the prior art generate a jerky transition between the functional elements acting in opposite directions precisely in this critical movement phase.

To avoid such a jerky transition, a freewheel can be provided for this movement phase of the tilting of the orthosis joint, in which neither of the functional elements exerts a force. However, the frictional connection is interrupted abruptly, which is associated with the fact that noises occur when the load on the functional elements is changed, which is also associated with wear.

Such known orthosis joints, e.g. as ankle joints, also only meet the cosmetic requirements to a limited extent due to the two projecting functional elements.

It is therefore the task of the present invention to provide a more compact and lighter orthosis joint compared to the prior art, which enables a natural-looking movement with extensive adjustment possibilities of a functional angle and with a physiologically initiated restoring force.

According to the invention, this task is solved by a joint with the features of the main claim. Advantageous embodiments and further developments of the invention are disclosed in the sub-claims, the description and the figures.

The orthosis joint according to the invention provides for generating the restoring force with only one functional element, which consists of at least one bending spring, which is oriented essentially longitudinally. By using only one bending spring, the orthosis joint can be made significantly smaller than the previously known embodiments.

In a preferred embodiment of the invention the bending spring is designed as a leaf spring, whereby in a particularly preferred embodiment this leaf spring has a stacking arrangement. In the context of the present invention, a stacking arrangement of this kind is understood to mean arranging a plurality of individual leaf springs, e.g. of different lengths, next to one another, i.e. stacking them so that the individual leaf springs are only used successively depending on the deflection.

Such a stacking arrangement also allows the leaf spring to be re-stacked within the orthosis joint as required, enabling the orthosis joint to be adapted or configured as needed. An additional range of special parts is not required. For this purpose, the orthosis joint according to the invention is equipped with a variable suspension or bearing of the individual leaf springs.

Although the use of bending springs in orthosis joints is known in principle, they have so far only been used for other purposes. For example, a polycentric orthosis joint is known from EP 1 768 620 B1, which is designed to generate a unilateral extension end stop for knee extension. For this purpose, various spacers are inserted between end stop surfaces, these spacers being held in position via leaf springs. A resilient restoring force acting on the two joint arms or on the limbs is not disclosed.

For the generation of the restoring forces, the actuation points in the orthosis joint according to the invention are arranged laterally to the side of the functional elements, i.e.

the bending spring or leaf spring or leaf spring arrangement in a triangular arrangement. When the joint arms are deflected in a first direction, at least three actuation points, which are found on the joint arms in the form of transmission elements, are displaced transversely to the longitudinal axis of the bending spring or leaf spring or leaf spring arrangement, causing the functional element to bend and thereby generating a restoring force.

This known principle of a triangular arrangement is basically applied once again in a mirrored form in the joint according to the invention. Due to different distances between the actuation points on the two sides of the functional element, the restoring forces may increase at different degrees.

A functional element can either lie parallel to a longitudinal axis of the orthosis joint, which is essentially defined by a limb to be used with the orthosis in an extended state, or be arranged perpendicular to this longitudinal axis. The transmission elements can be arranged on one side of the leaf spring arrangement and they can be pushed towards each other with respect to their distances. The restoring forces generated by the bending spring merge smoothly in each variant with alternating deflection.

There is a constant frictional connection between the joint arms on the orthosis joint and the functional element so that no jerky transition occurs due to the restoring force. The motion sequence possible with a joint according to the invention is thus comparable to a natural joint with the jerk-free and constant frictional connection to the muscles.

In the basic position, the functional element, i.e. the bending spring or leaf spring or leaf spring arrangement, is in a neutral position without internal tension. In this neutral position, it is easy to move the transmission elements, which are adjustably arranged on the joint arms, continuously along their longitudinal axis and then to fix them. In this way, the distance between the actuation points on the functional element can be changed, thereby altering the bending length and, in this context, the stiffness of the functional element, and thus the restoring force of the bending spring or leaf spring arrangement.

In a particularly preferred embodiment of the invention, one of the joint arms, in particular the second lower joint arm, has an articulated arm towards which it can be continuously rotated and locked in any angular position. The force transmission from the functional element to the second joint arm then occurs via this articulated arm. In particular, it is suggested that the articulated arm and the second joint arm be mounted on a common pivot point in order to create a loadable counter holder for clamping.

Another variant for this purpose provides for an additional latch between the articulated arm and the lower joint arm, which engages in at least one groove on the articulated arm in order to set one or more predetermined functional angles between the first and second joint arms.

Figure 2:
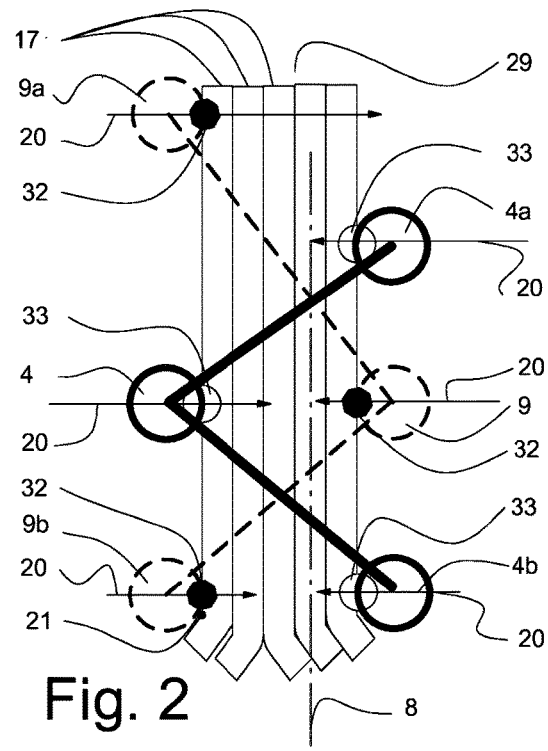
Figure 3:
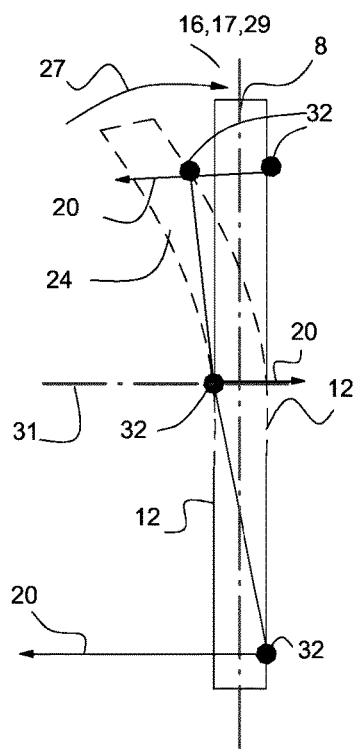
Figure 4:
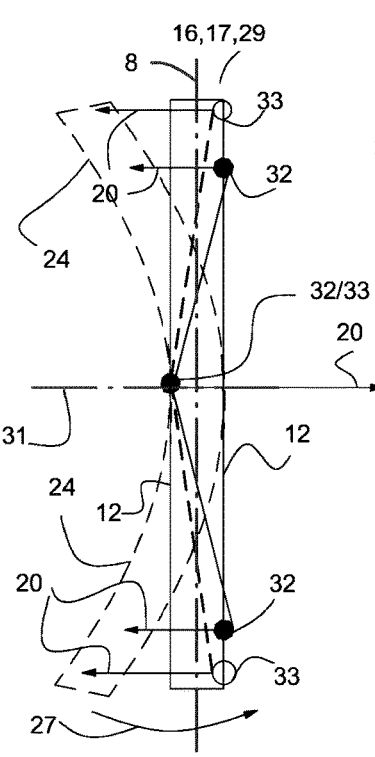
Figure 5:
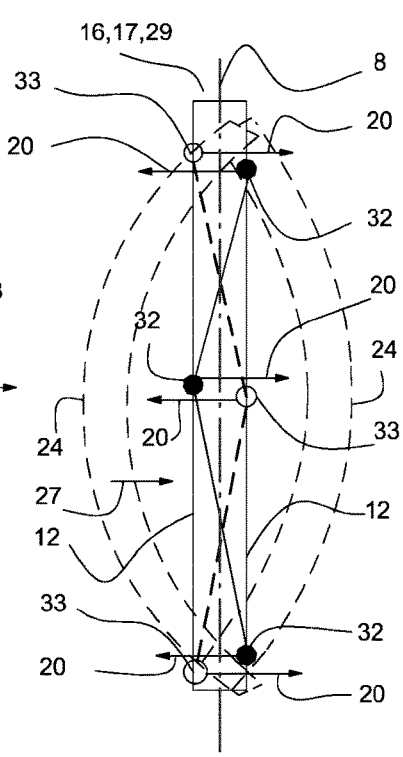

Further useful and/or advantageous features of the invention can be seen from the sub-claims and the following description of the drawing. Particularly preferred embodiments of the invention are explained in more detail with reference to the accompanying drawing. They show:

FIG. 1 the view of an exemplary bending spring and a leaf spring,

FIG. 2 the front view of an arrangement with leaf springs,

FIG. 3 the front view of a one-sided triangular arrangement of the actuation points with two-sided effect FIG. 4 the front view of an alternative one-sided triangular arrangement of the actuation points with two-sided effect, FIG. 5 the front view of a bilateral triangular arrangement of the actuation points with two-sided effect, FIG. 6 the front view of an orthosis joint in the neutral position, FIG. 7 the front view of an orthosis joint according to FIG. 6 in left-sided deflection, FIG. 8 the front view of an alternative embodiment of an orthosis joint e.g. as an ankle joint in left-sided deflection.

In the drawings, the same parts are largely marked with the same reference numerals.

FIG. 1 shows two embodiments of functional elements 29 according to the invention in the form of a bending spring 16 or a leaf spring 17, which are shown here in a straight aligned form, the leaf spring 17 featuring a frontal deflection 21 at one end. With this frontal deflection 21, a single spring can be suspended in a device to prevent a leaf spring 17 from slipping. Transmission elements 4, 4a, 4b, 9, 9a, 9b are also visible, as is the direction of a force transmission line 20, by means of which actuation points 32, 33 are formed on a transmission surface 12 located on the outside of the functional element 29, in particular laterally.

FIG. 2 shows a schematic front view of a functional element 29 for an orthosis joint 5 in the form of a leaf spring arrangement, consisting of several stacked leaf springs 17 arranged next to each other.

The functional element 29 is shown here schematically in the form of a preferred arrangement of leaf springs 17 and is mounted between the transmission elements 4, 4a, 4b, 9, 9a, 9b. During a deflection 24 of joint arms 1, 2 on which the transmission elements 4, 4a, 4b, 9, 9a, 9b are situated, forces are transmitted to the functional element 29 which are represented by the force transmission lines 20 transverse to a longitudinal axis 8 of the leaf springs 17. The transmission elements 4, 4a, 4b and the transmission elements 9, 9a, 9b are each shown in a triangular arrangement with connecting lines. This also shows the actuation points 32, 33 which are alternatively effective for deflections 24 in opposite directions. With corresponding deflections 24 of the joint arms 1, 2, restoring forces 27 are generated at the joint arms 1, 2, respectively, as explained further below with reference to FIGS. 7, 8.

FIG. 3 schematically shows a leaf spring 17 with only one triangular arrangement of the actuation points 32 for generating a restoring force 27. In this variant, only three actuation points 32 are mirrored around the mirror axis 31 on the force transmission line 20. The ends of the leaf spring 17 are actuated alternately. The advantage here is the very compact design. The restoring force 27 of the leaf spring 17 can be changed by shifting the center actuation point 32 parallel to the longitudinal axis of the leaf spring 17 to either side.

FIG. 4 shows a particularly preferred variant with a functional element 29 with two triangular arrangements formed with at least five actuation points 32, 33 for generating a restoring force 27. In this variant, the actuation points 32, 33 are mirrored on the mirror axis 31 of the force transmission line 20. The ends of the leaf spring 17 are deflected alternately, whereby two actuation points 32, 33 are alternately effective in the triangular arrangement.

FIG. 5 schematically depicts two triangular arrangements of the actuation points 32, 33 on a leaf spring 17 mirrored on the longitudinal axis 8. Here, the force on the force transmission line 20 for generating a bending and a restoring force 27 can be seen. A feature is the mirroring of six actuation points 32, 33 in two triangular arrangements on the longitudinal axis 8. The restoring force 27 generated alternatively in both directions can be changed by moving any of the actuation points.

FIG. 6 shows a schematic front view of an orthosis joint 5. Two triangular arrangements of the actuation points 32, 33 on a leaf spring 17 mirrored on the longitudinal axis 8 can be seen in accordance with FIG. 5.

The functional element 29 for generating a restoring force 27 is arranged here in the region of a pivot point 10 of the orthosis joint 5. The joint arms 1, 2, which are connected to each other at the pivot point 10, are clearly visible. Both joint arms 1, 2 can be pivoted to the right and left relative to one another. In this illustration, the functional element is in the neutral position 19, i.e. without deflection of the joint arms.

The lower joint arm 2 is mounted on the pivot point 10 together with an articulated arm 3 for setting a functional angle 14, depicted here, between joint arm 1 and joint arm 2. As can be seen, the angle between the joint arm 1 and the articulated arm 3 always remains unchanged, even if the joint arms 1 and 2 are pivoted against each other.

The articulated arm 3 can be continuously pivoted to either side of the center line relative to the articulated arm 2 and can be locked in place relative to the articulated arm 2 by a clamping element 22. The second joint arm 2 thus remains in frictional connection with the functional element 29 and with the first joint arm 1 via the articulated arm 3 at any set functional angle 14.

For each of the above triangular arrangements, transmission elements 4, 4a, 4b, 9, 9a, 9b are arranged on the first joint arm 1 with displacement elements 25 so that they can be adjusted and locked along the longitudinal axis 8 of the bending spring 16 or leaf spring 17. This allows the restoring force 27 of the functional element 29 to be changed.

A transmission element 9/23 positioned outside the range of the functional element 29 also allows a free deflection of the joint arm 1, 2 and disables the functional position and the restoring force 27.

A shaft applied as an eccentric 13 can be seen on the transmission element 9a. When the transmission element 9a is rotated about the eccentric 13, a limited freewheeling 23 of the transmission element in relation to the function element 29 can be set, in which the joint arm 1 is decoupled from the restoring force 27.

FIG. 7 shows a front view of an embodiment of the orthosis joint 5, depicted with a left-hand deflection 24 of the joint arms 1, 2, whereby the articulated arm 3 is simultaneously deflected to the right to generate a restoring force 27 on the leaf spring 17.

The principle with a double triangular arrangement of the actuation points 32, 33 is applied here mirrored about the longitudinal axis 8 of the functional element 29.

The arrangement of several leaf springs 17 shown, which are combined to form a stack of leaf springs, is clamped for deflection on both sides between six transmission elements 4, 4a, 4b and 9, 9a, 9b as shown in FIGS. 2, 5. For example, during the left-hand deflection 24 of the articulated arm 3 shown here, the individual leaf springs 17 are bent over the articulated arm 3.

When the joint arm 2 and the articulated arm 3 are deflected together, a rotatably mounted transmission element 4, 9 adjusts to the course of the leaf spring 17 or the stack of leaf springs in the example of an embodiment shown here.

By changing the distance between the transmission elements 4a, 9a and the transmission elements 4, 9, the active bending length of the arrangement of leaf springs 17 shown here is changed and thus produces a different course of the bending between the transmission elements 4, 9 and 4a, 9a with a resulting different restoring force 27.

For the adjustment of a functional angle 14, the clamping elements 22 are released so that the second joint arm 2 can be rotated in relation to the articulated arm 3. The second joint arm 2 can be continuously locked in the selected position via the clamping surfaces 11 between the shaft 7 and the articulated arm 3.

A predetermined adjustment of a functional angle 14 is possible with a bar 26 and at least one groove 28 on the articulated arm 3. In a simple embodiment of the joint 5 with limited adjustability of the functional angle 14, the transmission elements 4b, 9b and the transmission elements 4, 9 are thus arranged directly on the second joint arm 2. This means that the articulated arm 3 cannot be rotated relative to the second joint arm 2 and a functional angle 14 can only be set to a limited extent. The restoring force 27 on both sides is maintained.

FIG. 8 shows an alternative embodiment of an orthosis joint 5 as an ankle joint with left-side active deflection 24 of the joint arms 1, 2 and the articulated arm 3 to generate a restoring force 27 on the leaf spring 17. The principle is applied here with a triangular arrangement of the actuation points 32, 33 as shown in FIG. 4. The transmission elements 4, 4b and 9, 9b are arranged on the first joint arm 1. In the depicted left-hand deflection 24 of the articulated arm 3, the individual leaf springs 17 are bent over the articulated arm 3 at one end.

In this embodiment of the joint 5, the individual leaf springs 17 can be repositioned within the joint 5 against the outer edge of the transmission elements 4, 9, in accordance with the arrow 30, whereby the transmission elements 4, 9 are held in position between the leaf springs 17. These thus form configurable leaf springs 15. It is thus possible to configure the restoring force 27 of these leaf springs 15 for any body weight. Fine adjustments to the restoring force 27 are made by moving the transmission elements 4, 9 along the leaf spring 15.

The invention offers versatile possibilities and is not limited to the depicted embodiments of orthosis joints 5.

REFERENCE LIST 1. first, upper joint arm
2. second, lower joint arm
3. articulated arm
4. 4a, 4b transmission element
5. orthosis joint
6. center line joint
7. shaft
8. functional element longitudinal axis
9. 9a, 9b transmission element
10. pivot point
11. clamping surfaces
12. functional element transmission surface
13. eccentric
14. functional angle
15. configurable leaf spring
16. bending spring
17. leaf spring
20. force transmission line
21. deflection of a leaf spring
22. clamping element
23. freewheel
24. deflection with restoring force
25. displacement element 26. bolt
27. restoring force
28. groove
29. functional element
30. arrow
31. mirror axis
32. triangular arrangement of actuation points
33. triangular arrangement of actuation points

The invention claimed is:

1. An orthosis joint, comprising:
a first joint arm,
a second joint arm, wherein the first joint arm and the second joint arm are pivotable relative to one another to deflect in either of opposite directions from a basic position, and
at least one leaf spring which is configured to generate (i) a first restoring force in a first direction to restore one or more of the first arm and the second arm to the basic position from a first deflected position and (ii) a second restoring force in a second direction to restore one or more of the first arm and the second arm to the basic position from a second deflected position, wherein the second direction is opposite the first direction,
wherein the basic position forms an angle between the first and second joint arms at which the at least one leaf spring is configured to generate no restoring force, and
wherein an articulated arm is connected to the second joint arm in an adjustable and lockable manner for setting a functional angle between the first joint arm and the second joint arm, wherein force transmission from the at least one leaf spring to the second joint arm takes place only via the articulated arm.

2. The orthosis joint according to claim 1, wherein the at least one leaf spring comprises a stacking arrangement.

3. The orthosis joint according to claim 1, wherein at least three actuation points are arranged in a triangular arrangement on the at least one leaf spring for permitting the at least one leaf spring to generate the different restoring forces in opposite directions.

4. The orthosis joint according to claim 1, wherein at least one actuation point is adjustably arranged on one of the first joint arm and the second joint arm for changing the first or second restoring force.

5. The orthosis joint according to claim 1, wherein one or more of the first joint arm and the second joint arm is decouplable for a freewheel.

6. The orthosis joint according to claim 1, wherein the second joint arm is continuously lockable with the articulated arm via common clamping surfaces.

7. The orthosis joint according to claim 1, wherein the articulated arm comprises at least one groove for locking at the functional angle relative to the second joint arm.

8. The orthosis joint according to claim 1, wherein the articulated arm has a common pivot point with the first joint arm and the second joint arm.

* * * * *